US006614030B2

US 6,614,030 B2
\*Sep. 2, 2003

(12) United States Patent
Maher et al.

(54) MULTIPLEXED FLUORESCENT DETECTION IN MICROFLUIDIC DEVICES

(75) Inventors: Kevin Maher, Woodside, CA (US); Timothy F. Smith, Martinez, CA (US); Torleif Ove Bjornson, Gilroy, CA (US)

(73) Assignee: Aclara Biosciences, Inc., Mountain View, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 10/147,940

(22) Filed: May 15, 2002

(65) Prior Publication Data

US 2002/0179849 A1 Dec. 5, 2002

Related U.S. Application Data

(63) Continuation of application No. 09/569,963, filed on May 12, 2000, now Pat. No. 6,399,952.
(60) Provisional application No. 60/133,727, filed on May 12, 1999.

(51) Int. Cl.[7] .............................................. G01N 21/64
(52) U.S. Cl. .................................. 250/458.1; 250/461.1
(58) Field of Search ......................... 250/458.1, 459.1, 250/461.1, 462.2, 574; 356/317

(56) References Cited

U.S. PATENT DOCUMENTS

| 4,632,807 A | \* | 12/1986 | Marsoner ................. 422/82.08 |
| 5,296,703 A | | 3/1994 | Tsien |
| 5,436,718 A | \* | 7/1995 | Fernandes et al. ............. 356/73 |
| 5,571,410 A | | 11/1996 | Swedberg et al. |
| 5,587,128 A | | 12/1996 | Wilding et al. |
| 5,614,726 A | | 3/1997 | Kaye et al. |
| 5,630,924 A | | 5/1997 | Fuchs et al. |
| 5,730,850 A | | 3/1998 | Kambara et al. |
| 5,750,015 A | | 5/1998 | Soane et al. |

FOREIGN PATENT DOCUMENTS

WO    WO 98/49543    11/1998

OTHER PUBLICATIONS

Huang, C. et al. (1992). "DNA Sequencing Using Capillary Array Electrophoresis," *Analytical Chemistry* 64:2149–2154.
Khandurina, J. et al. (1999). "Microfabricated Porous Membrane Structure for Sample Concentration and Electrophoretic Analysis," *Analytical Chemistry* 71(9):1815–1819.
Kheterpal, I. et al. (1996). "DNA Sequencing Using a Four–Color Confocal Fluorescence Capillary Array Scanner," *Electrophoresis* 17:1852–1859.
Takahashi, S. et al. (1994). "Multiple Sheath–Flow Gel Capillary–Array Electrophoresis for Multicolor Fluorescent DNA Detection," *Analytical Chemistry* 66(7):1021–1026.
Woolley, A.T. et al. (1994). "Ultra–High–Speed Fragment Separations Using Microfabricated Capillary Electrophoresis Chips," *PNAS USA, Biophysics* 91(24):11348–11352.

\* cited by examiner

*Primary Examiner*—Scott J. Sugarman
*Assistant Examiner*—Richard Hanig
(74) *Attorney, Agent, or Firm*—Stephen C. Macevicz

(57) ABSTRACT

An optical detection and orientation device is provided comprising housing having an excitation light source, an optical element for reflecting the excitation light to an aspherical lens and transmitting light emitted by a fluorophore excited by said excitation light, a focussing lens for focusing the emitted light onto the entry of an optical fiber, which serves as a confocal aperture, and means for accurately moving said housing over a small area in relation to a channel in a microfluidic device. The optical detection and orientation device finds use in identifying the center of the channel and detecting fluorophores in the channel during operations involving fluorescent signals.

28 Claims, 9 Drawing Sheets

MULTIPLEXED FLUORESCENT DETECTION IN MICROFLUIDIC DEVICES

This application is a continuation application of patent application Ser. No. 09/569,963, filed May 12, 2000 now U.S. Pat. No. 6,399,952 which claims priority to Provisional Patent Application No. 60/133,727, filed May 12, 1999, each of which is incorporated herein by reference.

TECHNICAL FIELD

The field of this invention is fluorescent detection in microfluidic arrays.

1. Background

The combination of combinatorial chemistry, sequencing of the genomes of new species and relationships between genotype and physical and biological traits has greatly expanded the need to perform determinations of different events The multiplicity of new compounds that can be prepared using various forms of combinatorial chemistry and the numerous targets involving wild-type and mutated genes, had extraordinarily increased the number of determinations of interest in developing compounds having biological activity. These compounds include drugs, biocides, pesticide resistance, disease organism resistance and the like. In addition, the interest in discriminating between different genomes, relating specific mutations to phenotypes, defining susceptibilities to various environmental effects in relation to single nucleotide polymorphisms, and identifying the genomes of organisms to provide better defenses against the organisms has expanded the need for rapid inexpensive devices and methodologies for carrying out these and other determinations.

Recently, microfluidic arrays have been developed which allow for a multiplicity of reservoirs and channels to be associated with a small card or chip, where by using high voltages, various operations can be performed. The arrays provide for individual networks, which exist in combination on a single chip, so that a plurality of determinations may be performed concurrently and/or consecutively By having channels that have cross-sections in the range of about 500 to 5000 $\mu^2$, operations can be carried out with very small volumes In addition, by having very sensitive detection systems, very low concentration of a detectable label may be employed This allows for the use of very small samples and small amounts of reagents, which have become increasingly more sophisticated and expensive Micofluidic arrays offer the promise of more rapid throughput, increasingly smaller times to a determination and increasingly smaller amounts of sample and reagents being required The use of microfluidic arrays, however, is not without its challenges. The microfluidic arrays are desirably made in molded plastic, so as to provide a reduced cost of the chip. By molding the chip and providing for ridges on a mold to form the channels, the channels may not run true and may be displaced from their proper positions, as well as being slightly curved rather than perfectly straight. In addition, the plastic frequently autofluoresces. Since, the frequently used label is a fluorescent label, the signal from the label must be able to be distinguished from the autofluorescent signal. There is the problem of how to obtain a reliable fluorescent signal, in effect compromising maximizing the signal from the detectable label while minimizing the background signal.

In addition, the channel walls are not orthogonal to the cover plate, so that the depth of the irradiation will vary, depending upon the site of entry of the excitation beam into the channel. Where the excitation beam encounters the wall, the signal is degraded due to the reduced number of fluorophores which are excited and the excitation of the fluorophores in the wall. Therefore, precise positioning of the excitation beam in the channel is necessary for reproducible and accurate results.

2. Brief Description of Related Art

A number of patents have been published describing systems for detecting fluorescent signals in capillary arrays, such as U.S. Pat. Nos. 5,296,703 and 5,730,850, as well as WO98/49543.

SUMMARY OF THE INVENTION

An optical fluorescence detection system is provided for use with microfluidic arrays. The detection and orientation system comprises an optical train for receiving and processing light from a source of light and directing the light onto a microfluidic channel in a solid substrate. The optical train is moved across the surface of the solid substrate, crossing the channel and receiving the light emanating from the solid substrate. The optical train directs and processes the light from the solid substrate surface and directs the light to a detector. The signal from the detector is received by a data analyzer, which analyzes the signals and directs the optical train to the center of the channel in relation to the observed signals from the bulk material of the solid substrate, the edges of the channel and from the channel. Fluorescent components in the channel are detected by the fluorescence produced by the excitation light, where the emitted light is processed by the optical train and analyzed for the presence of fluorescence in the channel resulting from the fluorescent components in the channel, correcting for any fluorescence from the solid substrate.

The optical fluorescence detection system employs a plurality of miniaturized confocal microscope systems aligned in orientation with a plurality of channels of a microfluidic array. The systems are mounted on a movable support for alignment with sets of channels. The supports may be mounted on a carriage for alignment with different sets of channels. An irradiation unit comprises a source of light and processing means, such as lenses, dichroic mirrors, filters, gratings or the like, to reject light outside the wavelength range of interest. A single light source may be used and the beam split into a plurality of optical fibers for individual distribution of beamlets for channel irradiation. Similarly, the individual signals from each of the channels is directed by individual optical fibers to a common detector. Alternatively, individual light sources may be used for each confocal microscope system, such as LEDs or laser diodes.

The methodology allows for accurate, reproducible determination of a fluorescent signal from each of the channels. In order to achieve the desired sensitivity for detection, the center of each channel is determined, either when the channel is empty (air) or when a liquid is present, usually containing a fluorescent dye. Depending upon the degree of autofluorescence of the microfluidic array substrate, the optical system may look at fluorescent light, where there is sufficient autofluorescence to provide a detectable signal or scattered light, usually where the autofluorescence is low. In the case of scattered light, one would be detecting a different wavelength from the light, which would result from autofluorescence.

There are two different forms of delivering excitation: single mode fiber delivery or no fiber, where a laser and splitting must be done by discrete mirrors or a diffraction optical element; or multi-mode fiber delivery, where either a lamp or a laser may be used and splitting is done by homogenizing the laser or lamp light and then splitting using a multi-mode fiber array. The source of light will usually be a laser, generally being a laser producing a light beam having a wavelength in the range of about 250 to 800 nm, usually 488 nm, 532 nm or 633 nm.

Depending upon the source of light, such as a laser, a filter may be used to attenuate the intensity of the light to minimize photobleaching and photodestruction of the fluorescent labels. The light is then split into a plurality of rays or beamlets by a diffractive optical element, a combination of beam splitter elements, such as discrete mirrors, or other means, such as discrete beam splitters and fiber optic arrays. Each of the resulting beams is then directed to the individual confocal microscope associated with the channels. Either a single mode or multimode fiber may be employed, where one may use a multimode fiber optic array to split the illumination into N beamlets, where N is the number of optical trains to be illuminated. The fiber will generally have a diameter in the range of about 25 to 75 $\mu$m, particularly about 50 $\mu$m and a length in the range of about 1 to 1000 mm.

The confocal housing can be very compact, where the portion enclosing the optical train, usually in conjunction with other enclosed areas associated with the optical fibers and attachment to the orienting system, generally having a total volume of about 0.5 to $4 \times 10^4$ mm$^3$, with a cross-section in the range of 200 to 2000 mm$^2$ and a height in the range of about 25 to 200 mm. Each confocal microscope housing receives an individual light source optical fiber, with the fiber oriented such that the output face is normal to the optical axis of the housing and the light emerging is coincident with the optical axis. An optical system, usually involving a collimating lens and objective lens are positioned such that they focus the light from the fiber to a small spot. These lenses are usually aspherical with a single element. They are designed to be small, yet still offer diffraction limited performance.

Instead of having the optical fiber positioned at the optical axis, the chief ray from the optical fiber may be directed through a collimating lens which is outside the optical axis and collimates the light and directs the light to a dichroic mirror. The dichroic mirror directs the chief ray along the optical axis of the housing. The chief ray is focused by means of a lens with a high numerical aperture, generally in the range of about 0.25 to 0.75. The irradiation spot size will have a diameter of about 6–10 $\mu$m, while the collection area will be about 200 to 600 $\mu$m$^2$. The excitation light will excite fluorophores present in the channel at the detection site and the fluorescent light emitted from the channel will be collected by the high numerical aperture lens. When a collimating lens is used, the light will be directed past the collimating lens. By proper positioning and design of the collimating lens photon losses due to obscuration by the collimating lens will be minimized. Where the dichroic mirror is employed, the mirror will be substantially transparent in the wavelength range of interest and the light beam focussed by the focussing lens will pass through the dichroic mirror. After passing through the dichroic mirror or past the collimating lens, the light beam will usually be filtered to remove light outside the wavelength range of interest and be refocused onto a plane that contains the entrance aperture or core of a multimode optical fiber. The emission fiber will have substantially the same dimensions as the excitation fiber. The aperture acts as the confocal aperture for the confocal assembly, although there are other ways to provide the confocal pinhole, such as avalanche photodiodes, and other detectors. The emission beam is received and directed by the emission optical fiber to a detector. Various detectors may be employed which have the appropriate sensitivity, such as photomultiplier tubes (PMTs), charged coupled detectors (CCDs), avalanche photodiodes, etc. The signal may then be processed to provide the level of emission obtained from the channel and relate this intensity to the amount of fluorophore in the channel. Since the amount of fluorophore will relate to an event of interest, it may serve to identify the nature of the sample.

In some situations one will be interested in signals coming from different fluorophores having different wavelength ranges. The emission light beam may be split into the number of different wavelengths of interest, using filters, dichroic mirrors, prisms and the like. Various commercial systems are available for this purpose, such as prisms, beam splitter mirrors, etc. The subject assembly with the fiber preserves the laser light source mode and profile and assures optimal focussing of the ray on the sample by the confocal microscope assembly.

The housings may be used individually, but will usually be used in combination to read a plurality of channels at detection sites. The individual housings are mounted on a support, which will usually be mobile to allow for the support to move and reorient the housings in relation to different sets of channels. For example, with 8 housings, one may read 8 channels, and by being able to move the support one may read different groups of 8 channels, so that with 12 readings, one could read the samples from a 96 assay plate pattern. By having 12 housings or more, usually not more than about 96 housings, one could read a large number of samples quickly, since an individual reading would take less than a few seconds and the movement of the support would be automated and the entire set of readings would be performed in less than about a minute. The support allows for movement of the housings, so as to orient the beam to substantially the center of the channel. Various methods may be used for controlling the movement of the housings, including mechanical, electromechanical, electromagnetic, and the like. The different methods may involve anchoring the housing to an arm mounted on a pivot rod, where the arm is restrained in one direction and urged in the opposite direction, a voice coil actuator, where the lever arm extends into the center of the coil. By using a control rocker arm which is cam operated, or a movable support which moves in a plane, the housing can be moved up to about a distance of about 10–1000$\mu$, usually ⊕500 $\mu$, from a central point. Where the bulk material of the microfluidic chip is autofluorescence, the presence of the channel is determined by detecting the autofluorescence as one moves the illumination through a predetermined distance. With both autofluorescence and light scatter, where the bulk material is not significantly autofluorescent, there will be a channel signature as depicted to FIG. 9, showing the change in autofluorescent signal as the illumination traverses the channel.

The control arm is rigidly joined to the housing. The control arm is pivotally mounted on a bearing, so as to be able to move in a small arc about the channel. The arm can be actuated to scan the surface of the microfluidic chip about this arc, using the optical system for fluorescent detection to determine the site of the channel. Various actuators may be used for moving the arm and the housing, where the movement may be accelerated and decelerated as it passes through the arc. The observed autofluorescence is transmitted to the detector and the signals analyzed to determine the site of the channel. Once the borders of the channel have been determined, the housing and its optical axis may be oriented to be substantially above the center of the channel.

The length of the housing and lever arm will be relatively short, generally when measured from the axis of the bearing to the lens at the end of the housing adjacent to the microfluidic device, being in the range of 50 to 150 Movement of the housing will be controlled to at least steps of about 0.01µ, generally in the range of about 0.1 to 10µ.

Instead of using a mechanical arm, one may use various electromagnetic assemblies to control the movement of the housing in relation to an optical signal. By having opposing electromagnets or a single electromagnet with an opposing force, where the flux of the electromagnet is controlled by a computer, which relates the position of the housing to the change in signal as the housing traverses the channel area. Alternatively, one may use a motor and guide shaft for moving the housing, which allows the housing to traverse the channel area in a plane parallel to the surface of the chip.

Desirably one uses a single light source for a plurality of optical systems. The light from the single source is directed to a beam divider, such as a diffractive optical element or a system of beam splitters. Each of the beamlets is directed to an optical fiber which conducts the light to the optical system. While the light may be split into any number of rays, usually the total number of rays will not exceed 96, usually not exceed 64, more usually not exceed 32 and may be as few as 4, preferably from about 8 to 24. Each may be separated by an angle θ in a linear array, but a two dimensional array may also be formed with the appropriate angle between rays. Each ray has similar propagation parameters as the input beam. In particular, the divergence, and transverse intensity profile are preserved. When the transverse intensity profile of the light source is the "Gaussian" or $TEM_{00}$, then each ray will preserve this profile. This profile permits optimal focussing. Each ray is propagated a sufficient distance to provide separation and a distinct position. The distance will generally be at least 1 mm, usually in the range of about 1 to 1,000 mm. Individual lenses, such as aspherical lenses, achromatic doublets, etc., focus each ray into a single mode optical fiber. Each fiber is connected to one of the confocal microscope assemblies which is associated with each channel.

The microfluidic array will be in a solid substrate, which may be an inflexible substrate or a flexible substrate, such as a film. For examples of microfluidic devices, see, for example, U.S. Pat. No. 5,750,015. If flexible, it will usually be supported and oriented in conjunction with a rigid support. The channels comprising the detection site will generally have a depth of about 10 to 200 µm and a width at the opening of the channel in the range of about 1 to 500 µm, usually 10 to 200 µm. The channels may be parallel or in various arrays, where the inlet ports may be oriented in relation to a 96 or higher microtiter well plate, so that samples from the wells may be directly introduced into the port and microfluidic network. Depending on the purpose of the chip and the pattern of channels, whether the channels are straight, curved or tortuous, the chip may be only 1 or 2 cm long or 50 cm long, generally being from about 2 to 20 cm long, frequently 12.8 cm long. The width will vary with the number and pattern of channels, generally being at least about 1 cm, more usually at least about 2 cm and may be 50 cm wide, frequently about 8.5 cm wide. The chips will have inlet and outlet ports, usually reservoirs for buffer and waste which are connected to the channels and there may be additional channels connected to the main channel for transferring sample, reagents, etc., to the main channel. Electrodes will be provided for the channels, where the electrodes may be part of the chip, painted with electroconductive paint or metal plated on the chip, or electrodes may be provided for introduction into the reservoirs or channels by an external device. The spacing between the channels will usually be at least about 0.5 mm, more usually at least about 1 mm, at the detection site. Since the channels may take many courses and shapes, the distance between two adjacent channels may vary.

In order to make a series of determinations in the chip the chip is introduced into a module or group of modules, which will include the movable support. The chip will be indexed in relation to the support, so that the channels will be substantially oriented in relation to the optical axis of the associated housings. The module may also include electrodes or connectors to electrodes which are part of the chip, containers or other instrumentality, e.g. syringes, capillaries, etc., which can serve as sources of reagents, sample, and the like, which provide for fluid transfer through the ports in the chip, electrical connections between the fluorescent detectors and a data analysis system, and the like. The various modules are combined, so as to receive the chip and orient the chip in relation to the various components which interact with the chip. Indexing may be provided on the chip, so as to be locked in a predetermined position in relation to the module and the support. Prior to initiating operation in the channel, the housings are oriented in relation to the centers of the channels. Each of the housings is individually moved across the plane of the microfluidic chip intersecting the channel at the detection zone. Depending upon the level of autofluorescence of the composition of the substrate, autofluorescence or scattered light may be read. Where there is significant autofluorescence, autofluorescence or scattered light may be detected and read. Where the autofluorescence signal is low, scattered light will be read.

Where scattered light is being detected, the scatter will be different at the edges of the channel, as compared to the scatter from the channel. By observing the change in the scattered light, as the housing moves across the plane of the microfluidic chip, one can detect the transition from the edges of the channel to the channel and select the center as equally distant from the edges.

Once the housings are fixed in registry with the channel, the orientation process need not be repeated in relation to the channel and optical housing and numerous readings may be taken. One may then perform various operations, where a fluorophore label is brought to the detection site. The detection of the fluorophore label may be as a result of a competition assay, nucleic acid sequencing, immunoassays, etc.

DESCRIPTION OF THE SPECIFIC EMBODIMENTS

Figure 1:
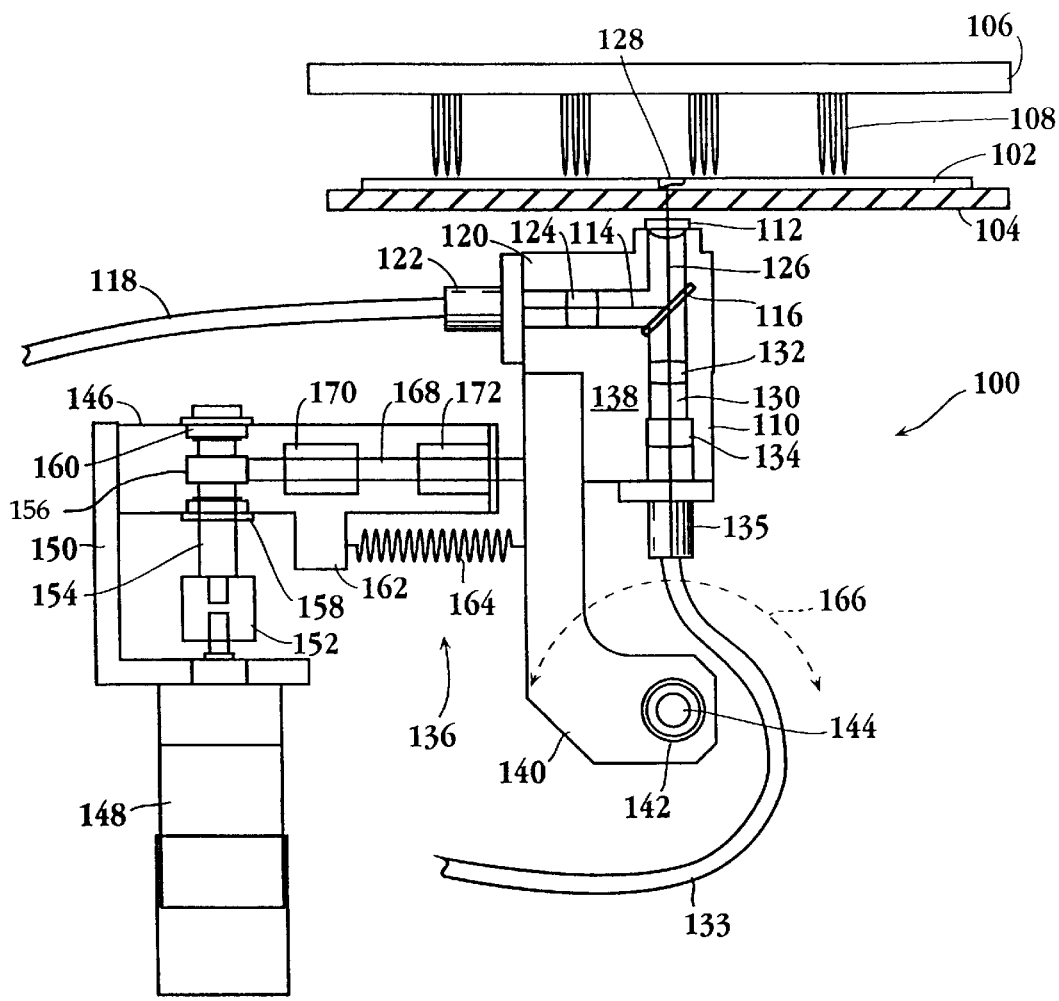
FIG. 1 is an elevational side view of an optical detection system.

For further understanding of the invention, the drawings will now be considered. In FIG. 1 is depicted a detection station 100. In conjunction with the detection station is a microfluidic chip 102, held in position by a quartz plate 104. The quartz plate may be part of a vacuum chuck, not shown, whereby the microfluidic chip 102 is held in fixed registry in relation to the detection station 100. Other ways of maintaining the microfluidic chip in place include gravity, force pins, pressure, clips, reversible adhesives, etc. Also depicted is an electrode lid 106 with electrodes 108, where the electrodes 108 can extend into ports of the microfluidic chip 102, during operation of electrokinetic processes. As described above, the microfluidic chip 102 will have a plurality of channels, where the system for only one channel is shown. The detection station has optical housing 110, which is a small tubular housing, which may be made of any convenient material, e.g., plastic, aluminum, steel, etc., and will desirably have the minimal dimensions necessary for housing the various components of the optical system. The optical system, to the extent permissible, will employ miniaturized optical elements, such as diffractive optical elements, DOEs. A single DOE may serve a plurality of functions, such as acting as a lens, mirror and/or grating, where the component will be about 3 mm×3 mm. The optical system includes an aspherical lens 112 at one end of the housing in apposition to the channel in the microfluidic chip, which aspheric lens 112 directs the excitation beam to the center of the channel after appropriate orientation, as described below. An excitation light beam 114 is directed to dichroic mirror 116 or equivalent optical element by means of optical fiber connected to arm 120 of housing 110 by means of coupler 122. Light beam 114 passes through a lens 124, which serves to collect the divergent light from the fiber. The excitation beam 114 is then reflected by dichroic mirror 116, which reflects light of the excitation wavelength of interest and allows light outside the reflective wavelength to pass through the dichroic mirror. The internal walls and all supporting elements will desirably be black, so as to maximize scattered light absorption. The reflected light beam 126 is focussed by aspherical lens 112 and forms a sharp small beam which passes through the support plate 104 into channel 128. When fluorophore is in the channel 128, the fluorophores will be excited and emit light which will exit the channel 128 and be collected by the aspherical lens 112. The emission beam will pass through the dichroic mirror 116, filter 132, to reject light outside the wavelength range of interest and lens 134 which focuses the light beam 130 on the entry of collection optical fiber 132. The optical fiber is attached to the housing 110 by means of coupler. The collection optical fiber 132 transfers the photons to a detector, not shown.

The housing 110 is affixed to the orientation device 136 by means of flange 138. Flange 138 is bonded to and connects together as a movable unit housing 110, arm 120 and lever 140. Lever 140 is rotatably mounted on bearing 142 which is supported by axle 144. The orientation device 136 comprises a tubular casing 146 which is fixedly attached to the encoder unit 148 by L-bar 150. The casing 146 and motor unit 148 and held in fixed relationship, so that movement of the lever arm 140 can be accurately controlled and the position of the lever arm 140 and in this way the housing 110 readily determined. The encoder 148 is connected by connector 152 to the rod 154 on which cam 156 is fixedly mounted. Rod 154 passes through bearings 158 and 160, which are set in tubular casing 146, so as to maintain rod 154 in place and allow for rotation of cam 156 from a fixed axis of rotation. The tubular housing 146 has a fin 162 to which one end of a spring 164 is attached, being attached at the other end to lever arm 140. The spring 164 restrains lever arm 140 and urges the arm 140 in the direction of the fin 162 or in the counter-clockwise direction as indicated by broken line 166. Bar 168 is supported by bushings 170 and 172 and its length provides for a tight fit between the cam 156 and the contact position on lever arm 140. Therefore, the distance between the surface of the cam 156 on which the bar 168 is displaced and the lever arm 140 remains constant. As the cam 156 rotates, the bar 168 is extended or retracted in relation to the rod 154 on which the cam is journaled. As the lever arm 140 responds to the movement of the bar 168, the optical system in housing 110 scans the surface for the fluorescence being emitted. As indicated previously, there will be a substantial drop at the borders of the channel 128 in the microfluidic chip 102. By knowing the position of the borders and the distance between the borders, the encoder can be controlled to move the bar 168 to center the housing 110 over the center of the channel 128. Once the housing is centered over the channel, the electrokinetic determination may be made and the change in fluorescence monitored in the channel 128, with the change in signal resulting from the change in fluorescence intensity directed by collection fiber 132 to a data collection and analysis device, not shown.

The microfluidic chip may be oriented so as to have a single channel within the confines of the width of a single housing so that the determination of the channel center is orthogonal to the channel. Alternatively, the channel may be at an angle to the path of the housing, so that the measurements are at an angle to the channel boundaries, still allowing for the center to be determined. Instead of having the housings in a row, the housings may be organized in any manner which allows them to determine the boundaries of the channel at the detection site, such as forming an arc, an equally spaced apart array with a number of columns and rows, or other pattern in relation to the pattern of the detection sites of the channels to be monitored.

Figure 2:
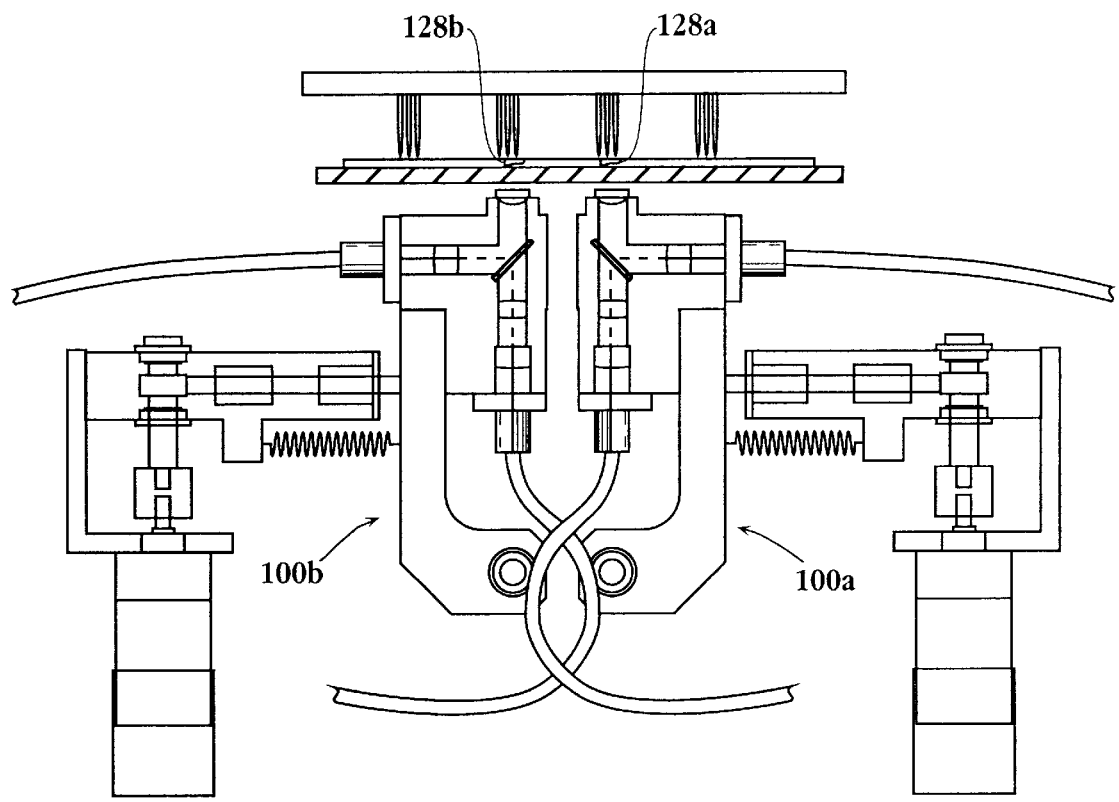
FIG. 2 is an elevational side view of a pair of optical detections systems.

In FIG. 2 is shown an analogous device as depicted in FIG. 1, except that there are two complete units which are confronting and monitor two different channels. In this arrangement, one has two rows of devices. Since all of the parts are the same, the same numbering has been used to indicate the different components. The two detection stations 100a and 100b confront each other over channels 128a and 128b. Each of the detection stations 100a and 100b move independently of each other having their own orientation devices 136a and 136b, respectively. By having two sets of optical detection stations, one doubles the number of readings that can be performed at the same time. Where the channels are orientated properly, the two rows of optical detection stations monitor two sets of channels and provide data more rapidly.

Figure 3:
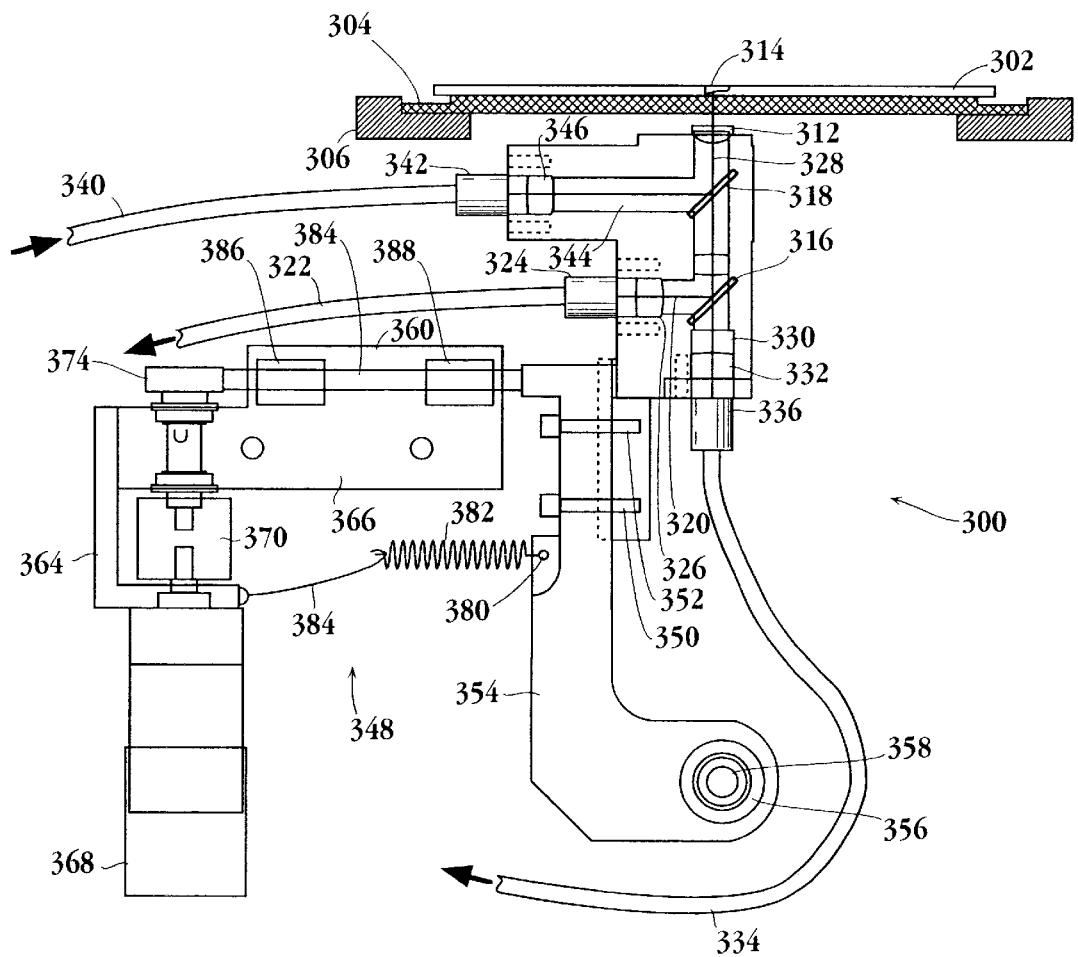
FIG. 3 is an elevational side view of an alternative optical detection system.

In FIG. 3, a modified structure is provided, which can be used in two ways: in a first way, it allows for identifying fluorophores having different absorption wavelengths; and in a second way employs a single wavelength, but uses a different path for detection of scatter from the microfluidic chip. The figure also provides a different mechanical structure for the orientation device. The optical detection device 300 has microfluidic chip 302 held in position by glass plate 304 in vacuum chuck 306. The microfluidic chip 302 is held in fixed registry in relation to the detection station 300. An electrode lid or other electrode source, not shown, is provided for the voltage across the channels of the microfluidic chip 302. The detection station has optical station 310, which is a small tubular housing, which will be at least about 3 mm OD, more usually, at least 5 mm OD and usually not more than about 15 mm OD, more usually not more than about 10 mm OD. Desirably, the spacing center-to-center of the housings in a row will be from about 6 to 12 mm, more particularly 8 to 10 mm. The housing may be made of any convenient material, metal or plastic, with the minimal dimensions required containing the optical train and providing the desired specifications. The optical system, to the extent permissible, will employ miniaturized optical elements, such as diffractive optical elements. The optical system includes an aspherical lens 312 at one end of the housing in apposition to the channel 314 in the microfluidic chip 302. The aspherical lens 312 directs the excitation beam to the center of the channel after appropriate orientation. It also serves to transmit a small light beam for detection of the boundaries of the channel 314. The housing has two dichroic mirrors, an upper dichroic mirror 316 and a lower dichroic mirror 318. The two mirrors find use for using two different wavelengths for excitation of fluorophores. An upper excitation light beam 320 is directed to upper dichroic mirror 316 or equivalent optical element by optical fiber 322 connected to housing 310 by means of coupler 324. Light beam 320 passes through a bandpass filter 326, which rejects light out of a first wavelength range of interest. The excitation light beam 320 is then reflected by dichroic mirror 316, which reflects light within the wavelength light of interest and allows emitted light of the wavelength of interest to pass. The internal walls and supporting elements are desirably black. The reflected light beam 328 is focussed by aspherical lens 312 to a sharp small beam, desirably in the range of about 5 to 25 $\mu$m. The irradiation beam excites fluorophores in the channel at the detection site and light is emitted. By having a beam of about 10 $\mu$m in diameter, with a channel of about 50 $\mu$m in width and 100 $\mu$m in depth, the volume which is irradiated is about *. For a 50 pM concentration of fluorophores, the number of molecules which are irradiated are *. The emitted light passes through dichroic mirrors 318 and 316 through filter 330, which rejects light outside of the wavelengths of the two different fluorophores and is focussed by objective lens on the entry of collection optical fiber attached to housing 310 by coupler. The entry of the collection optical fiber 334 serves as the confocal aperture. In analogous manner lower optical fiber 340 is connected to housing 310 through coupler 342 and directs a light beam 344 of a different wavelength from light beam 320 through bandpass filter 346. The light beam 344 acts analogously to light beam 320, being reflected by dichroic mirror 318 into the channel 314, where fluorescent light is emitted, collected and focussed by aspherical lens 312 and directed through both dichroic mirrors 318 and 316 to the confocal aperture provided by the entry to multimode optical fiber 334.

For determining the center of the channel 314, an orientation mechanism 348 is provided, which is substantially the same as the orientation mechanism of FIG. 1. The housing 310 is affixed to the orientation device 348 by means of bolts 350 and 352. The bolts extend through lever arm 354. In this way housing 310 is secured to and connects together as a movable unit housing 310 and lever 354. Lever 354 is rotatably mounted on bearing 356 which is supported by axle 358. The orientation device 348 comprises a tubular casing 360 which is fixedly attached to the encoder unit 362 by L-bar 364 and flange 366. The casing 360 and encoder unit 368 are held in fixed relationship, so that movement of the lever arm 354 can be accurately controlled and the position of the lever arm 354, and in this way the housing 310, can be readily determined. The encoder 368 is connected by connector 370 to the rod 372 on which cam 374 is fixedly mounted. Rod 372 passes through bearings 376 and 378, which are set in flange 366, so as to maintain rod 372 in place and allow for rotation of cam 374 from a fixed axis of rotation Lever arm 354 has pin 380 to which spring 382 is attached, where the other end of spring 382 is affixed to a hook 384 attached to L-bar 364 The spring 382 restrains lever arm 354 and urges the arm 354 in the direction of the L-bar. Bar 384 is supported by bushings 386 and 388 and its length provides for a tight fit between the cam 374 and the contact position on lever arm 354. Therefore, the distance between the surface of the cam 374 on which the bar 384 is displaced and the lever arm 354 remains constant. As the cam 374 rotates, the bar 384 is extended or retracted in relation to the rod 372 on which the cam is journaled. As the lever arm 354 responds to the movement of the bar 384, the optical system in housing 310 scans the surface for the fluorescence being emitted. As indicated previously, there will be a substantial drop at the borders of the channel 314 in the microfluidic chip 302. By knowing the position of the borders and the distance between the borders, the encoder can be controlled to move the bar 384 to center the housing 310 over the center of the channel 314. Once the housing is centered over the channel, the electrokinetic determination may be made and the change in fluorescence monitored in the channel 314, with the change in signal resulting from the change in fluorescence intensity directed by collection fiber 334 to a data collection and analysis device, not shown.

In the second use of the device, optical fiber 340 provides the excitation light, which is reflected to the microfluidic chip 302. The dichroic mirror 316 collects the scatter light and transmits that light to a collection optical fiber 322. Both dichroic mirrors 316 and 318 are transparent to the fluorescent signal emitted from the channel 314, which fluorescent light is transmitted to optical fiber 334 for processing by a data processor.

In the next series of figures, the common elements to the figures will not be repeated. They provide an environment for the different devices for moving the housing to identify the site of the channel center.

Figure 4:
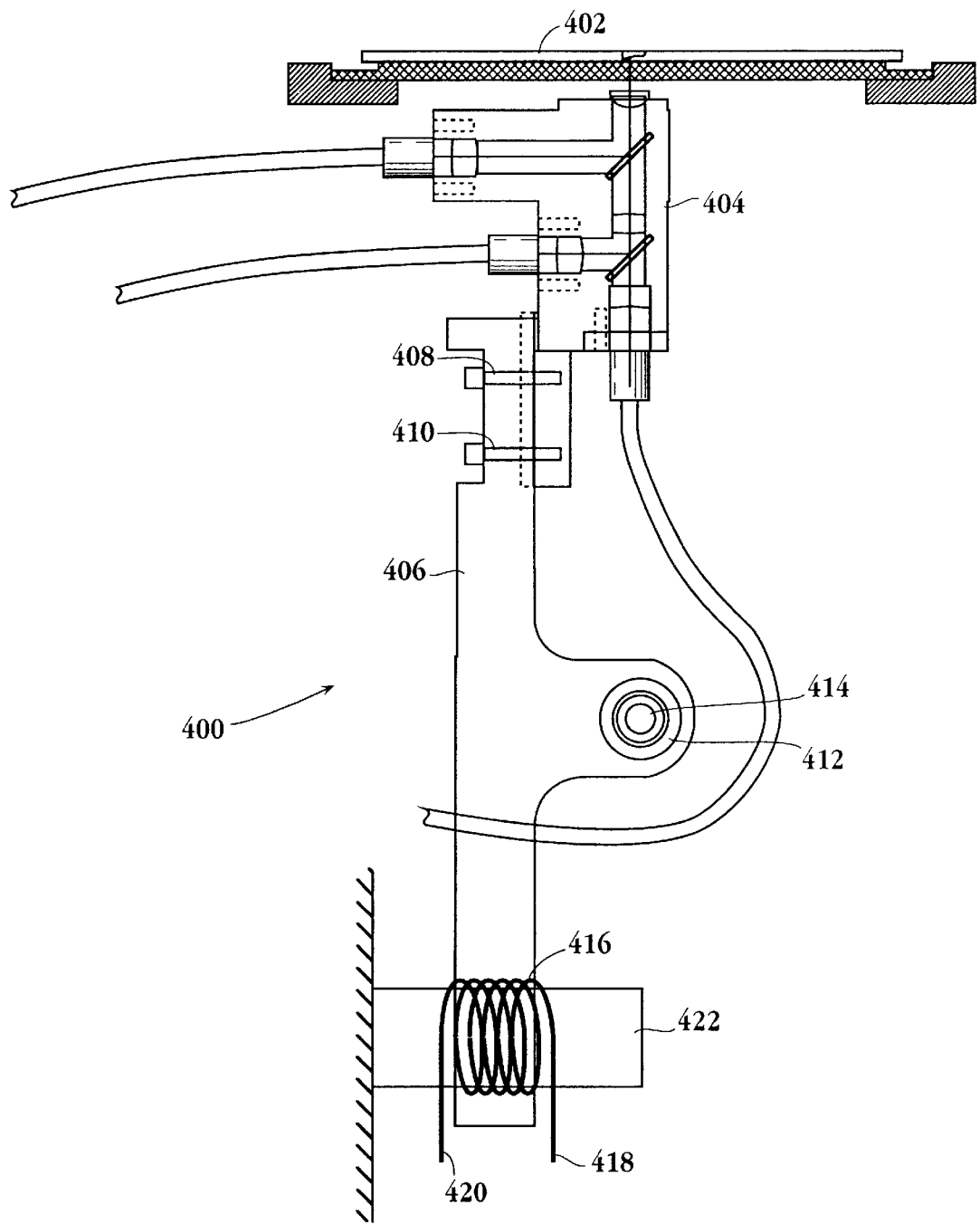
FIG. 4 is an elevational view of an alternative embodiment using an electromagnetic actuator for orienting the optical detection system.

In FIG. 4, the device 400 is associated with microfluidic chip 402, and has optical station 404, which includes the same optics as described in FIG. 3 for housing 310. Optical station 404 is fastened to arm 406 by set screws 408 and 410. Arm 406 has bearing 412, which is mounted on pivot rod 414. Arm 406 terminates in electrical coil 416 which has leads 418 and 420. A magnetic bar 422 extends through coil 420. The leads are connected to a source of dc current, not shown, which is controlled by a data analyzer, also not shown. The signal from optical system 404 is sent to the data analyzer, which detects the change in signal as the housing traverses the plane of the microfluidic chip 402 and identifies the center of the channel. The data analyzer changes the current in the coil to move the arm 406 to scan the surface of the microfluidic chip 402. When the center of the channel is identified, the data analyzer fixes the position of the housing to direct the excitation light to the center of the channel.

Figure 5:
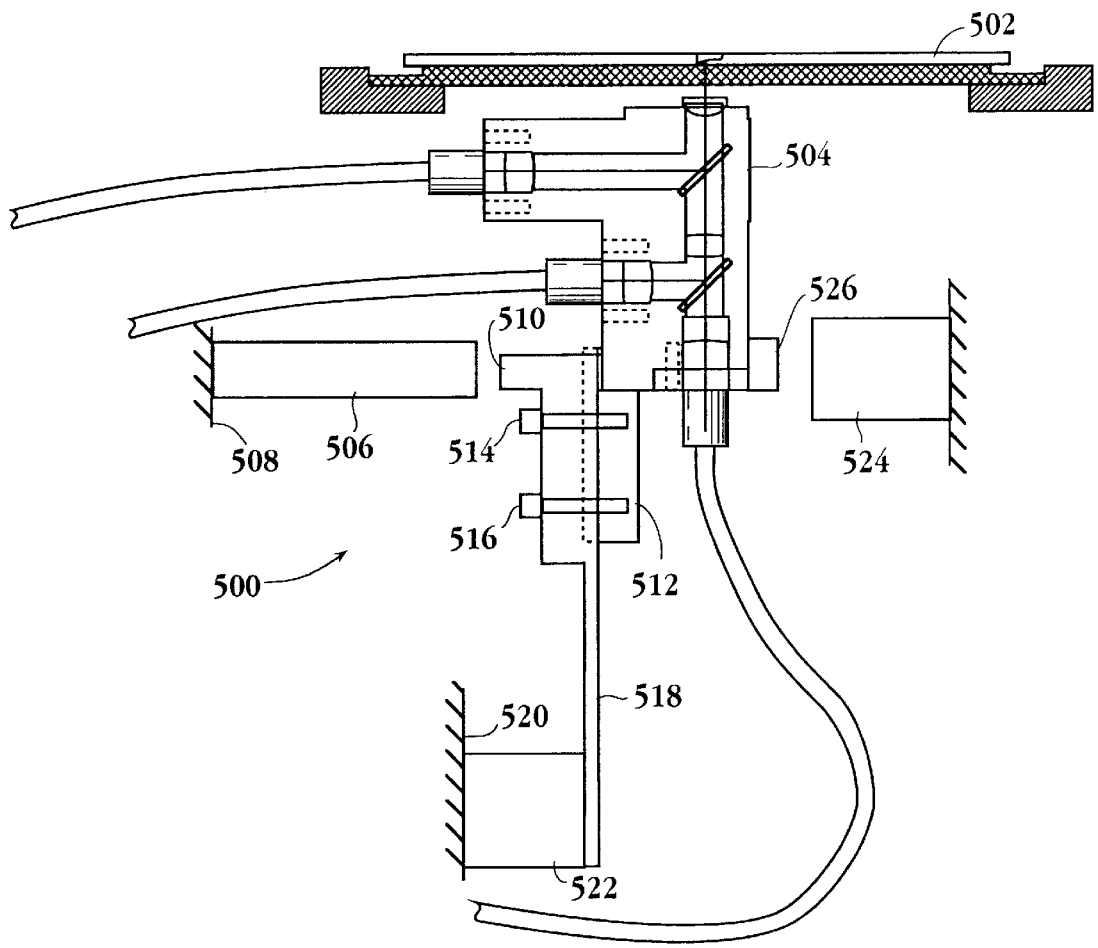
FIG. 5 is an elevational view of an alternative embodiment using a second manner of using an electromagnetic actuator for orienting the optical detection system.

In FIG. 5, an alternative electromagnetic device is employed. The device 500 is associated with microfluidic chip 502 and has optical station 504, which includes the same optics as described in FIG. 3 for housing 310. An electromagnetic actuator 506 rigidly affixed to a support 508 and confronts iron surface 510. The housing 504 is attached at flange 512 by means of bolts 514 and 516 to a flexible pivot arm 518 which is affixed to support 520 by bar 522. When the electromagnetic acuator 506 is activated by applying a current to the electromagnetic actuator 506, a field is produced which attracts the iron surface 510 toward the electromagnetic actuator 506. The flexible pivot arm 518 bends and applies a restraining force against the movement of the housing 504 toward the electromagnetic actuator 506. By varying the magnetic flux of the electromagnetic actuator 506, the housing 504 will move in an arc across the plane of the microfluidic chip 502, allowing for detecting the center of the channel as a result of the change in signal resulting from the light emanating from the channel. A position resolver 524 confronts surface 526, where the position resolver 524 detects the position of the housing 504. The position resolver 524 may determine the distance between it and surface 526 using sound or optics. Once the center of the channel has been determined by a data analyzer, the signal from the position resolver 524 related to the position of the housing 504 directing light to the center of the channel can be recorded and the housing 504 restored to that position for each determination in that channel. In this manner one need not scan the surface each time one wishes to have a determination, but may rely on the signal from the position resolver 524 to determine when the housing is properly positioned.

In the next two figures, the housing is mounted on a carrier which moves in a plane parallel to the surface of the microfluidic chip, so that the light incident from the housing is always in the same direction onto the microfluidic chip.

Figure 6:
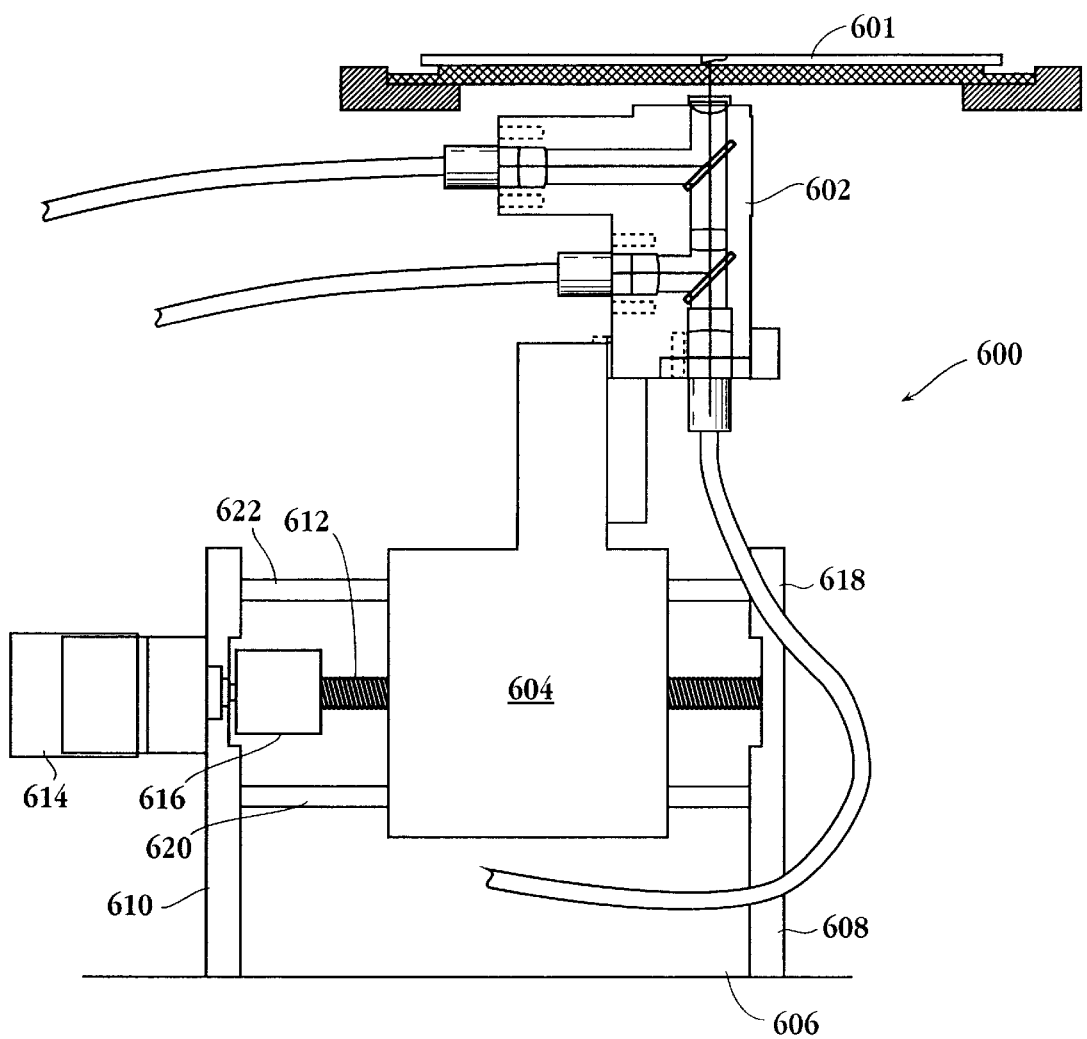
FIG. 6 is an elevational view of an alternative embodiment using a mechanically moved carrier in a plane parallel to the microfluidic substrate for orienting the optical detection system.

In FIG. 6, the device 600 has a microfluidic chip 601 under optical system 602 mounted on movable carrier 604. Movable carrier 604 is mounted on stand 606, which has two confronting support posts 608 and 610, respectively. The movement of movable carrier 604 is controlled by lead screw 612 which passes through a threaded channel in movable carrier and is turned by motor 614 connected to lead screw 612 by coupler 616. Lead screw 612 is supported in post 608 by bearing 618. Two guide shafts 620 and 622 extend between posts 608 and 610 and pass through smooth channels in movable carrier 604 to maintain the movement of movable carrier 604 in the same plane. The motor 614 is controlled by a data analyzer, which controls the movement of movable carrier 604 and receives signals from optical system 602. When the center of the channel is detected, the movement of the movable carrier is stopped and maintained in the same position.

Figure 7:
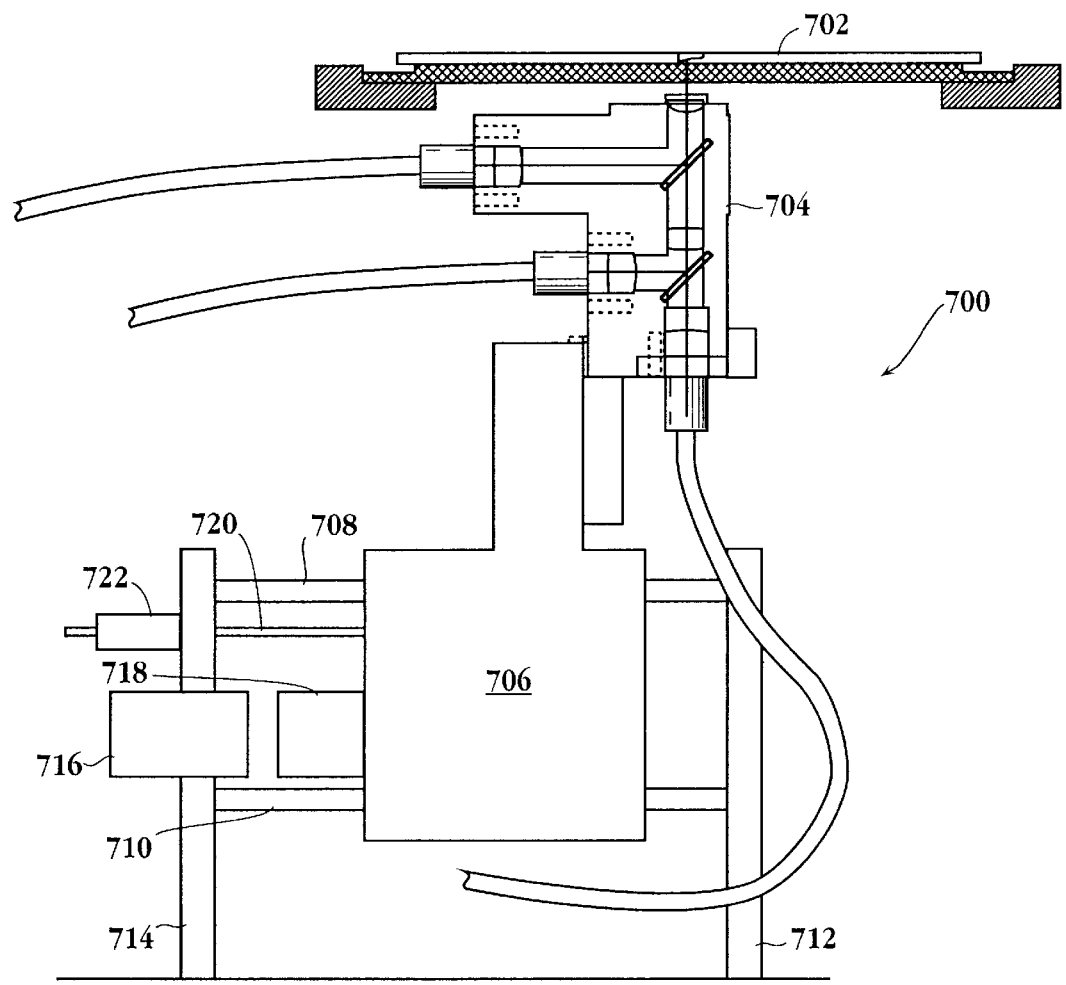
FIG. 7 is an elevational view of an alternative embodiment of using an electromagnetic actuator for moving a carrier in a plane parallel to the microfluidic substrate for orienting the optical detection system.

In FIG. 7, the device 700 uses an electromagnetic actuator for controlling the movement of optical system. In order to maintain the optical system in a linear plane parallel to the surface of the microfluidic chip, one uses one or more linear guides, such as a guide shaft, guide bearing, etc. The device 700 has microfluidic chip 702 and optical system 704 which is mounted on movable carrier 706. As in FIG. 6, movable carrier 706 is guided by guide shafts 708 and 710 which extend between the posts 712 ands 714 and pass through smooth channels in movable carrier 706 to maintain the travel of movable carrier 706 in a constant plane parallel to the upper surface of the microfluidic chip 702. Mounted on post 714 is electromagnetic actuator 716. Mounted on the side of movable carrier 706 confronting electromagnetic actuator 716 is bar magnet 718. By varying the strength and polarity of the field of electromagnetic actuator 716, the movable carrier 706 can be moved back and forth along the guide shafts 708 and 710. A detection rod 720 is attached at one of its ends to movable carrier 706 and extends through post 714 and position resolver 722. The detection rod 720 is position coded, such as a graduated change in color, transparency, reflectivity, or the like, so that the portion of the detection rod 720 in the position resolver 722 may be accurately determined. Once the appropriate position of the detection rod 720 is determined the movable carrier 706 can always be brought back to the same site for further monitoring of the channel in the microfluidic chip 702. By having signals from the optical system 704 sent to a data analyzer which also monitors the position of the detection rod 720, the center of the channel in the microfluidic chip can be related to the position of the detection rod 720, when the optical system is situated at the center of the channel.

Figure 8:
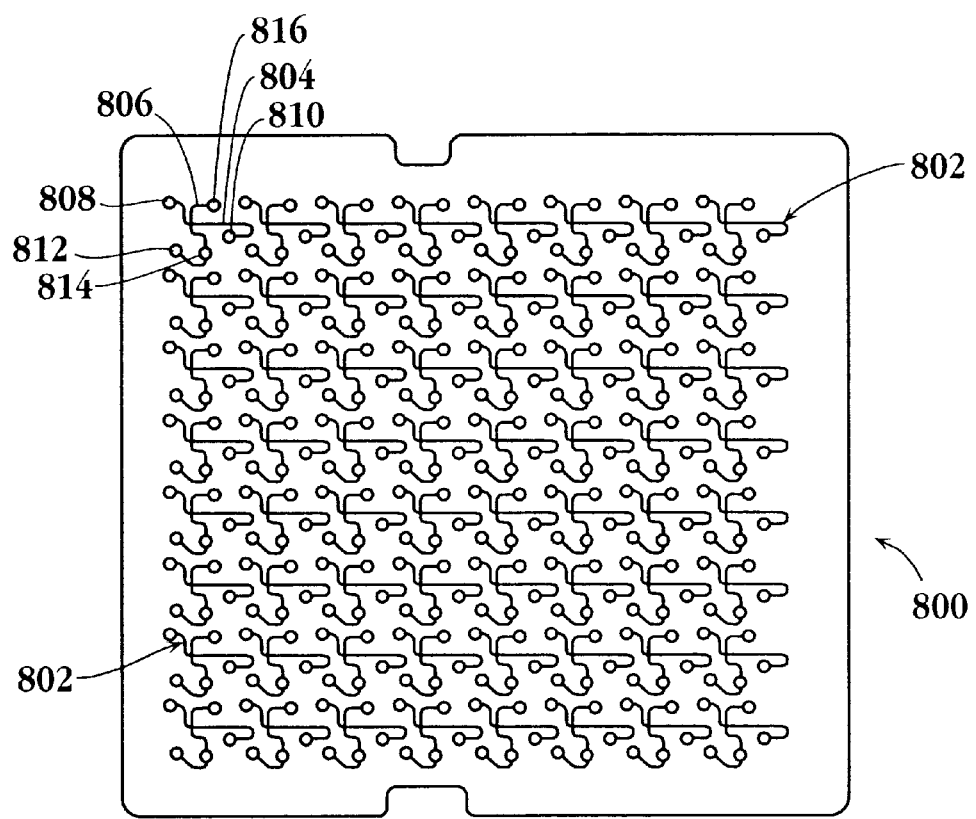
FIG. 8 is a top view of the surface of a microfluidic chip in which a plurality of channel networks is featured.
Figure 9:
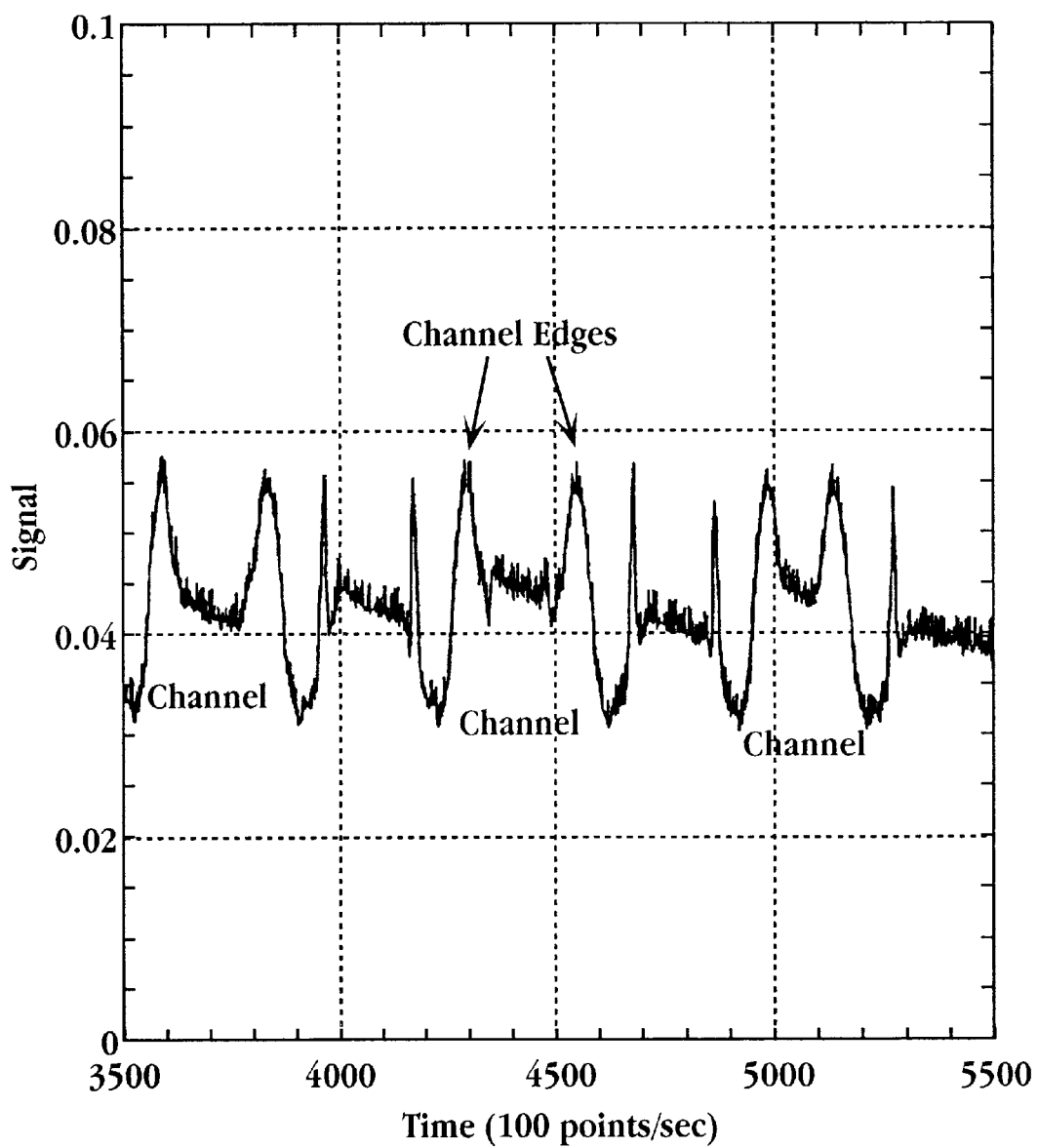
FIG. 9 is a graph of the observed signal when orienting the optical system in relation to a channel. The conditions under which the determination was run are: laser power 2 mW; spot size 10 microns at FWHM; acrylic microfluidic chip, 30 microns deep channel, 80 microns wide filled with HEPES buffer (50 mM, pH 7.4); scan across open channel (back and forth) at approx. 400 microns/sec; Mini-Confocal Optical System with 488 nm excitation (Argon-Ion laser), 530 nm emission filter, 30 nm FWHM bandpass; focus nominally set for optimum signal performance.

As previously indicated, the channels may take many patterns in a microfluidic chip. In FIG. 8 is a diagrammatic top view of the surface of a microfluidic chip 800. A plurality of channel networks 802 have main channel 804, cross-channel 806 with ports and reservoirs 808 and 810 for the main channel 804 and ports and reservoirs 812 and 814 for the cross-channel 806. The channel networks 802 are spaced apart in an arc and the "X"s 816 indicate the detection sites on the main channels 804 at which the optical housing is positioned. Instead of an arc, the channel networks could be distributed to define a circle, where the optical housings could be mounted on a platform, which allows a group of the housings to rotate to address different groups of channel networks.

If desired, various electrode patterns may be made part of the microfluidic chip, which may be connected to a computer or other data analyzing device, which serves to control the voltages at the various electrodes during the course of the operation. In addition, the computer may serve to control the optical detection device positioning during the operation.

As described previously, the microfluidic device will have a plurality of channels, where depending on the number of channels, all of the channels may be simultaneously addressed by an equal number of optical detection devices or a portion of the number of channels may be addressed at any one time and the optical detection device or microfluidic chip or both moved in relation to each other to permit the optical detection device to address a plurality of different channels. For example, with a microfluidic chip which has 96 channels, each port intended to receive a sample from a well of a 96 microtiter well plate, one may have 8 or 12 optical detection devices in a unit to monitor an equal number of channels. After monitoring an equal number of channels, the optical detection device unit and/or microfluidic chip would then be moved to address a different set of channels and the procedure repeated until all of the channels had been monitored.

It is evident from the above results that the subject invention provides for an improved manner of detecting fluorophores in microchannels. The device and methods greatly enhance the signal, as well as the signal-to-noise ratio, and permit rapid determination of a large number of samples, so that at a single time numerous channels may be monitored. The mechanisms employed can be miniaturized, so as to be compact, while being able to address a plurality of microchannels in a small space. Various designs of channels are compatible with the detection system Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An optical detection and orientation system for irradiating a sample material in at least one microchannel wherein said microchannel is in a solid substrate, said system comprising:
    at least one source of excitation light optically coupled to a movable optical train, said optical train comprising at least one optical element configured to direct said excitation light from said at least one source to said microchannel;
    a carrier, said optical train being supported by said carrier and said carrier being adapted to move said optical train relative to said solid substrate;
    at least one optical element configured to receive light emanating from said microchannel and transfer said emanating light to at least one detector; and
    a data analyzer configured to analyze and control movement of said carrier based on said emanating light.

2. An optical detection and orientation system according to claim 1, wherein said movable optical train is adapted to scan across the surface of said solid substrate having a plurality of microchannels to be detected.

3. An optical detection and orientation system according to claim 1, wherein said emanating light is fluorescent light.

4. An optical detection and orientation system according to claim 1, wherein said emanating light is scattered light.

5. An optical detection and orientation system according to claim 1, wherein said at least one light source is not part of said optical train.

6. An optical detection and orientation system according to claim 5, wherein said at least one light source is optically coupled to said optical train via an optical fiber.

7. An optical detection and orientation system according to claim 5, wherein said emanating light is collimated.

8. An optical detection and orientation system according to claim 1, comprising a plurality of light sources.

9. An optical detection and orientation system according to claim 8, wherein one of said plurality of light sources is one of a lamp, laser, LED and laser diode.

10. An optical detection and orientation system according to claim 1, wherein said at least one light source emits a wavelength in the range of 250 to 800 nm.

11. An optical detection and orientation system according to claim 1, wherein said at least one light source emits light at one of 488, 532, and 633 nm.

12. An optical detection and orientation system according to claim 1, wherein said excitation light is collimated.

13. An optical detection and orientation system according to claim 1, wherein said carrier is adapted to pivot.

14. An optical detection and orientation system according to claim 1, wherein said carrier is adapted to move linearly.

15. An optical detection and orientation system according to claim 1, wherein said excitation light irradiates a spot on said solid substrate having a diameter in a range of 6–10 microns.

16. An optical detection and orientation system for irradiating a sample material in a microchannel, wherein said microchannel is in a solid substrate, said system comprising:
    at least one source of excitation light;
    a movable optical unit comprising a housing accommodating an optical train, a reflective and transmissive optical element for directing an excitation light beam from said at least one source to an aspherical lens, which aspherical lens focuses the light on said microchannel and collects the light emanating from said microchannel and focuses and directs the emanating light through said reflective and transmissive optical element, wherein said reflective and transmissive element reflects said excitation light beam and transmits said emanating light;
    a carrier, said housing being attached to said carrier;
    a moving means affixed to said carrier for moving said carrier and unit relative to said solid substrate;
    a focusing lens for receiving said emanating light and directing a focused beam of emanating light on the entry of an optical fiber, wherein said entry serves as a confocal aperture; and
    a connector from said optical fiber to a data analyzer, said data analyzer for analyzing changes in light emanating from said solid substrate as said carrier and unit move relative to said solid substrate, and said data analyzer configured to control said moving means based on receiving said emanating light.

17. An optical detection and orientation system according to claim 16, comprising means for orienting said substrate in a fixed position relative to said housing.

18. An optical detection and orientation system according to claim 16, wherein said carrier is a rotatable lever arm.

19. An optical detection and orientation system according to claim 18, wherein said moving means comprises a rotating cam mounted on a motor driven axle, a bar positioned between said cam and said housing, and a restraining means connected to and urging said movable optical unit toward said axle.

20. An optical detection and orientation system according to claim 16, wherein said carrier is a support, which moves on a linear guide.

21. An optical detection and orientation system according to claim 20, wherein said support is moved by mechanical forces.

22. An optical detection and orientation system according to claim 20, wherein said support is moved by electromagnetic forces.

23. An optical detection and orientation system according to claim 16, further comprising a data analysis unit for receiving the signals from said emanating light and controlling said moving means for moving said optical unit.

24. An optical detection and orientation system according to claim 16, further comprising a filter between said focusing lens and said reflective and transmissive element for filtering light outside of the wavelength range of interest of said emanating light.

25. An optical detection and orientation system according to claim 16, wherein said movable optical train is adapted to scan across the surface of said solid substrate having a plurality of microchannels to be detected.

26. An optical detection and orientation system according to claim 16, wherein said excitation light irradiates a spot on said solid substrate having a diameter in a range of 6–10 microns.

27. An optical detection and orientation system according to claim 16, wherein said movable optical train is adapted to scan across the surface of said solid substrate having a plurality of microchannels to be detected.

28. An optical detection and orientation system for irradiating a sample material in a microchannel, wherein said microchannel is in a solid substrate, said system comprising:

at least one source of excitation light;

a movable optical unit comprising a reflective and transmissive optical element for directing an excitation light beam from said at least one source to an aspherical lens, which aspherical lens focuses the light on said microchannel and collects the light emanating from said microchannel and focuses and directs the emanating light through said reflective and transmissive optical element, wherein said reflective and transmissive element reflects said excitation light beam and transmits said emanating light;

a carrier device which is adapted to move in at least one movement of pivot movement and linear movement, said optical unit being attached to said carrier device;

a focusing lens for receiving said emanating light and directing a focused beam of emanating light on the entry of an optical fiber, wherein said entry serves as a confocal aperture; and a connector from said optical fiber to a data analyzer, said data analyzer for analyzing changes in light emanating from said solid substrate as said carrier and unit move relative to said solid substrate, and said data analyzer configured to control said movement based on receiving said emanating light.

* * * * *